(12) United States Patent
Czarnek (10) Patent No.: US 7,370,819 B2
(45) Date of Patent: May 13, 2008

(54) DEVICE AND METHOD FOR GRINDING BIOLOGICAL SAMPLES

(75) Inventor: Robert Czarnek, Johnstown, PA (US)

(73) Assignee: Advanced Analytical Technologies, Inc., Ames, IA (US)

(*) Notice: Subject to any disclaimer, the term of this patent is extended or adjusted under 35 U.S.C. 154(b) by 63 days.

(21) Appl. No.: 11/527,152

(22) Filed: Sep. 26, 2006

(65) Prior Publication Data

US 2007/0262181 A1  Nov. 15, 2007

Related U.S. Application Data

(60) Provisional application No. 60/800,472, filed on May 15, 2006.

(51) Int. Cl.
 *B02C 19/00* (2006.01)
(52) U.S. Cl. .................. 241/2; 241/21; 241/169.1; 241/199.12
(58) Field of Classification Search ............ 241/2, 241/169.1, 169, 199.12, 21
See application file for complete search history.

(56) References Cited

U.S. PATENT DOCUMENTS 4,307,846 A * 12/1981 Spelsberg ............... 241/246
5,390,859 A * 2/1995 Rajasekaran ............ 241/2
5,829,696 A * 11/1998 DeStefano et al. ....... 241/169

OTHER PUBLICATIONS

Joseph Edward Shigley: "Mechanical Engineering Design"; Second Edition; McGraw-Hill Book Company; copyright 1963, 1972; (6 pp.).

* cited by examiner

*Primary Examiner*—Mark Rosenbaum
(74) *Attorney, Agent, or Firm*—The Webb Law Firm (57) ABSTRACT

In a biological sample grinding device and method, a bearing having a plurality of rolling elements disposed between a pair of rings is disposed in a container in which a fluid having at least one biological sample particle therein is introduced. With the bearing immersed in the fluid having the biological sample particle therein, one ring of the bearing is rotated relative to the other ring thereof, whereupon the rolling elements roll between the pair of rings and, in response thereto, the biological sample particle is drawn by the fluid between the pair of rings where it is subject to being crushed or ground between at least one of the rolling elements and at least one of the rings. A baffle can be disposed in the container for inhibiting the rotation of the fluid and, hence, the introduction of air into the fluid.

20 Claims, 8 Drawing Sheets

DEVICE AND METHOD FOR GRINDING BIOLOGICAL SAMPLES

CROSS REFERENCE TO RELATED APPLICATION

The present invention claims priority from U.S. Provisional Patent Application No. 60/800,472, filed on May 15, 2006, the contents of which are incorporated herein by reference.

BACKGROUND OF THE INVENTION

1. Field of the Invention

The present invention relates to preparation of a biological sample for testing.

2. Description of Related Art

Biological contamination of in-process materials and finished goods occurs. Current quality control and quality assurance practices employ traditional microbiology techniques that are labor intensive and often require a 3-14 day incubation time before contamination can be detected. Contamination can occur as individual growing cells, as in the case of bacteria, or as clusters or clumps of cellular growth in the form of a network of hyphae, in the case of mold. Before the latter sample can be tested for presence or absence of contamination, the clumps of growth must be broken up into individual cells or small fragments.

Several methods of breaking up a sample have been tried with various successes. Specifically, heretofore, small homogenizers, shakers with metal balls and other mechanical means of cutting or breaking up the sample into pieces have been implemented. Even though the sample was broken up into small fragments, the results were, in most cases, unacceptable because either the fragments were not uniform, the time required to fragment the sample was too long, or debris generated by the grinding device introduced background material that masked the detection of the real sample.

It would, therefore, be desirable to provide a device and method of breaking up biological samples for the detection of biological contamination that produce results superior to all previous devices and methods, whereupon: each sample is more uniform; the generation of debris is avoided; sample preparation time is reduced; and the noise associated with sample preparation is reduced.

SUMMARY OF THE INVENTION

The invention is a biological sample grinding device. The device includes a vial having a conical or concave interior surface, a shaft, and a bearing having a plurality of rolling elements disposed between a pair of surfaces in contact therewith. The rolling elements define at least one gap therebetween. The bearing is mounted to the shaft and disposed in the vial such that one surface of the bearing is rotatable in concert with the shaft, while the other surface of the bearing is held stationary against the rotation of the shaft via the interior surface of the vial. At least one biological sample particle disposed in a fluid in which the bearing is submerged in the vial enters the at least one gap between the rolling elements whereupon, in response to rotation of the shaft, the biological sample is subject to being crushed or ground between at least one rolling element and at least one of the pair of surfaces.

The bearing can be a ball bearing, a needle bearing, or a roller bearing.

The device can further include means for rotating the shaft and the one surface of the bearing about a longitudinal axis of the shaft. A baffle can be disposed in the vial such that during rotation of the shaft and the one surface of the bearing, the baffle inhibits the rotation of the fluid in the vial. The baffle can be either (1) a sheet having at least one fold or (2) at least a partial cylinder having a plurality of inwardly extending projections.

The bearing can include a bore which is press fit to the shaft to mount the bearing to the shaft. Each surface of the bearing can be defined by a race formed in a ring of the bearing.

The invention is also a method of grinding a biological sample. The method includes providing a container and inserting a bearing in the container. The bearing includes a plurality of rolling elements disposed between a pair of rings of the bearing. A fluid having at least one biological sample particle therein is introduced into the container. With the bearing immersed in the fluid having the biological sample particle therein, one ring of the bearing is caused to rotate relative to the other ring of the bearing such that the rolling elements roll between the pair of rings whereupon, in response to the rotation, the biological sample particle is drawn by the fluid between the pair of rings where it is subject to being crushed or ground between at least one of the rolling elements and at least one of the rings.

The rotation direction of the one ring of the bearing can be reversed at least one time.

The one ring is an inner ring of the bearing while the other ring is an outer ring of the bearing, which is held stationary in the container, desirably, via an interior wall of the container and, more desirably, via frictional interaction between the outer ring and the interior wall of the container.

The method can further include inserting in the container a baffle that is operative for avoiding the introduction of air into the fluid in response to the rotation of the one ring of the bearing relative to the other ring of the bearing. The baffle can be either (1) a sheet having at least one fold or (2) at least a partial cylinder having a plurality of inwardly extending projections.

Lastly, the invention is a biological sample grinding device that includes a vessel for receiving a fluid having at least one biological sample particle therein; a bearing disposed in the vessel, the bearing having a plurality of rolling elements disposed for rolling between a pair of coaxial, radially opposed surfaces; and means for rotating one of the bearing surfaces relative to the other of the bearing surfaces when the bearing is submerged in the fluid received in the vessel whereupon, in response to the rotation, the biological sample particle is drawn by the fluid between the pair of surfaces where the biological sample particle is crushed or ground between at least one of the rolling elements and one of the pair of surfaces.

The pair of surfaces can include a first surface that faces radially outward and a second surface that faces radially inward. The means for rotating can rotate the first surface while the second surface can be maintained stationary via a wall of the vessel when the means for rotating is rotating the first surface.

A baffle can be disposed in the vessel and operative for inhibiting the introduction of air into the fluid during rotation of the first surface.

The means for rotating can reverse the direction of rotation of the first surface one or more times. The means for rotating can include a motor driven shaft coupled to a ring that defines the first surface.

The vessel can have a conical or concave interior surface. A ring can define the second surface. A part of the ring other than the second surface can frictionally engage the conical or concave interior surface, thereby avoiding rotation of the second surface when the means for rotating rotates the first surface.

DETAILED DESCRIPTION OF THE INVENTION

The present invention will be described with reference to the accompanying Figs. where like reference numbers correspond to like elements.

Figure 1:
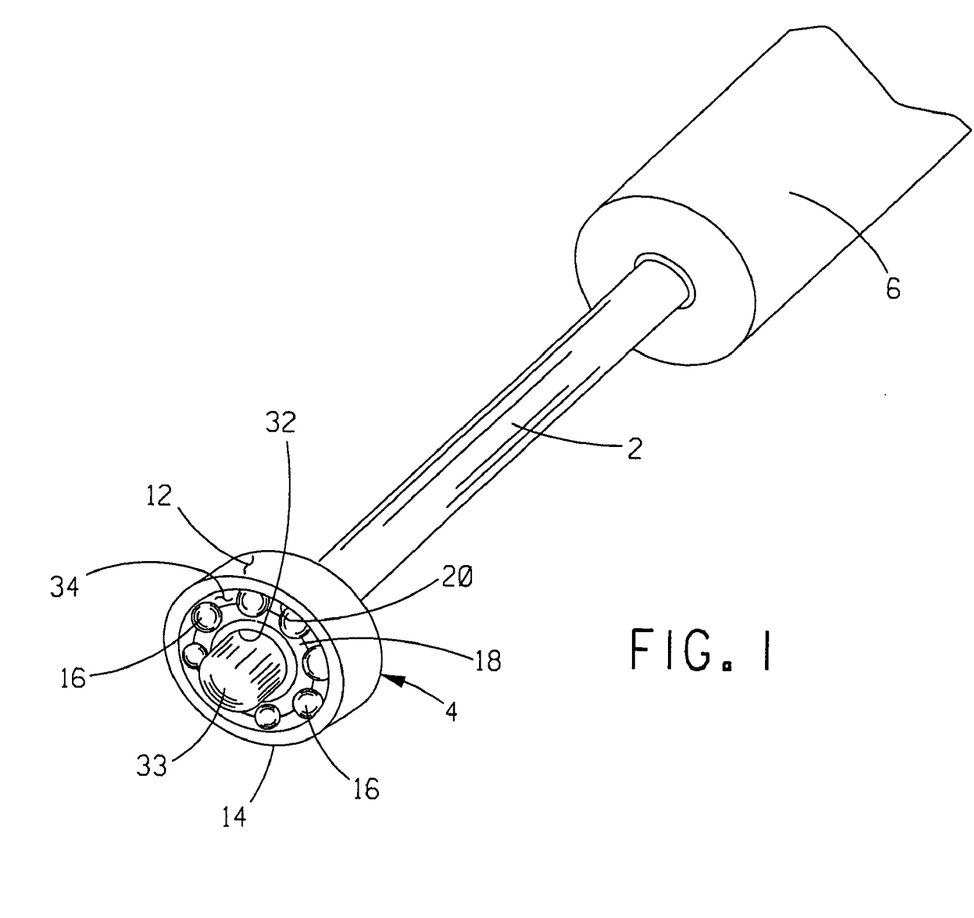
FIG. 1 is a perspective view of a shaft having a ball bearing and a motor coupled to opposite ends thereof.
Figure 2:
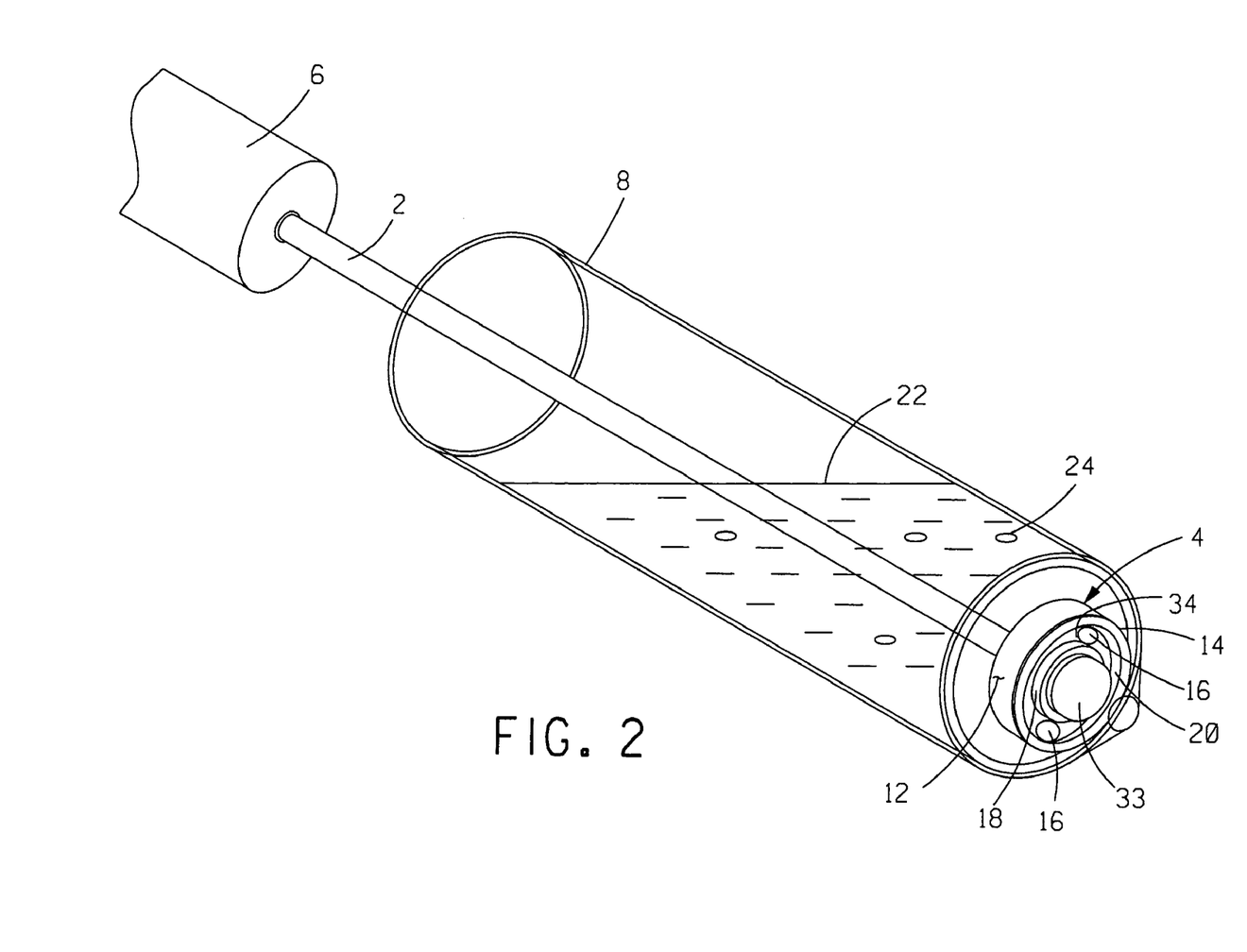
FIGS. 2 and 3 are perspective views of the shaft and ball bearing of FIG. 1 disposed in a vial that contains a transport fluid in which biological sample particles are received.
Figure 3:
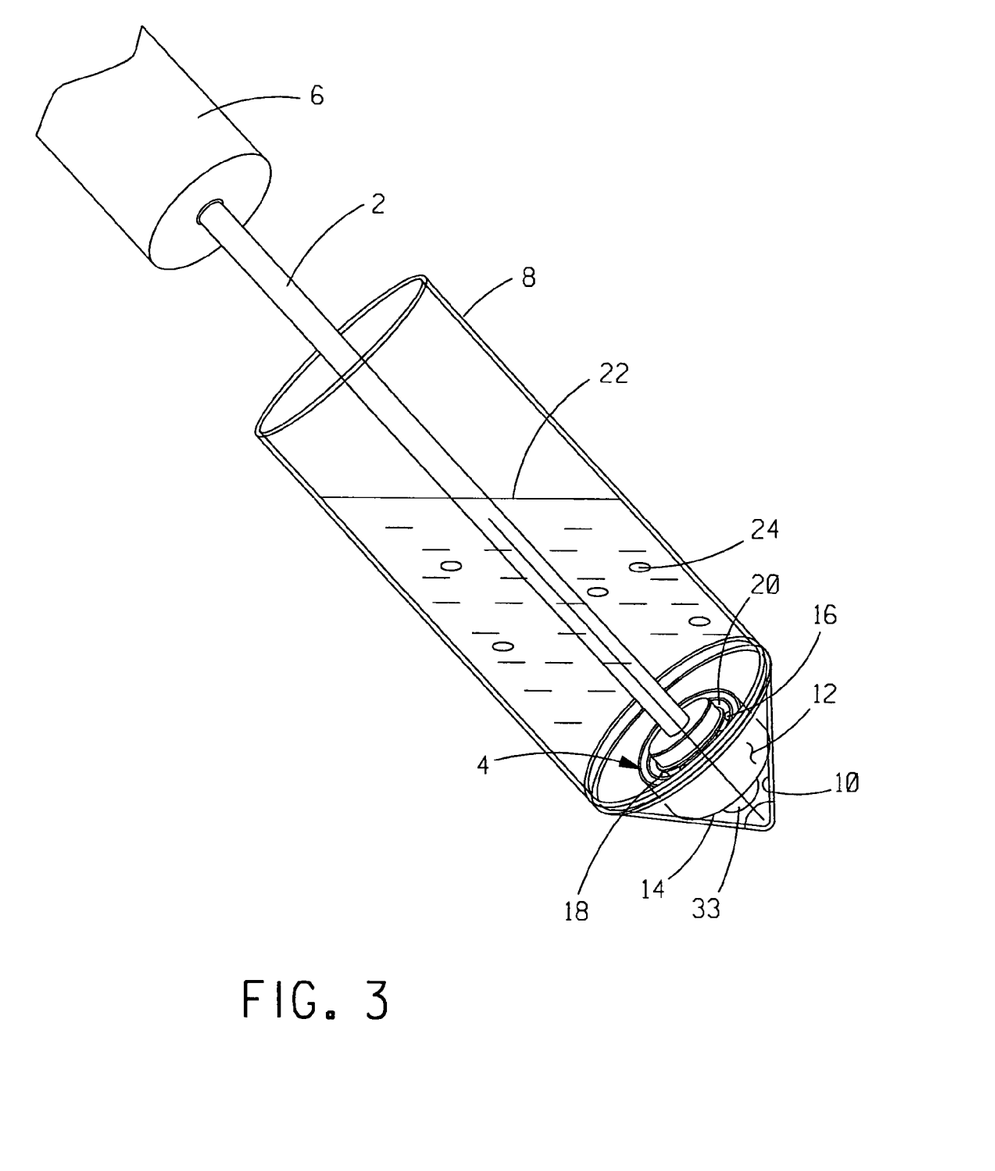

With reference to FIG. 1, a grinding device in accordance with one embodiment of the present invention includes a ball bearing 4 mounted on a shaft 2, desirably adjacent one end thereof, and a drive mechanism 6, such as an electric motor, coupled to shaft 2, desirably adjacent the other end thereof. Drive mechanism 6 is operative for causing shaft 2 to rotate about its longitudinal axis.

With reference to FIGS. 2-5 and with continuing reference to FIG. 1, the ball bearing 4 end of shaft 2 is inserted in an open end of a sample vial 8 having a conical or concave-shaped interior bottom wall 10 opposite the open end thereof. At least part of an outer ring 12 of ball bearing 4 is pressed into contact with bottom wall 10 of vial 8 via an axial force applied to shaft 2. More specifically, a corner radius or edge 14 of outer ring 12, desirably the whole perimeter of corner radius 14, is pressed into contact with the conical or concave-shaped surface of bottom wall 10 with sufficient force to restrict the rotation of outer ring 12 by way of frictional interaction between edge 14 and the surface of bottom wall 10.

Figure 4:
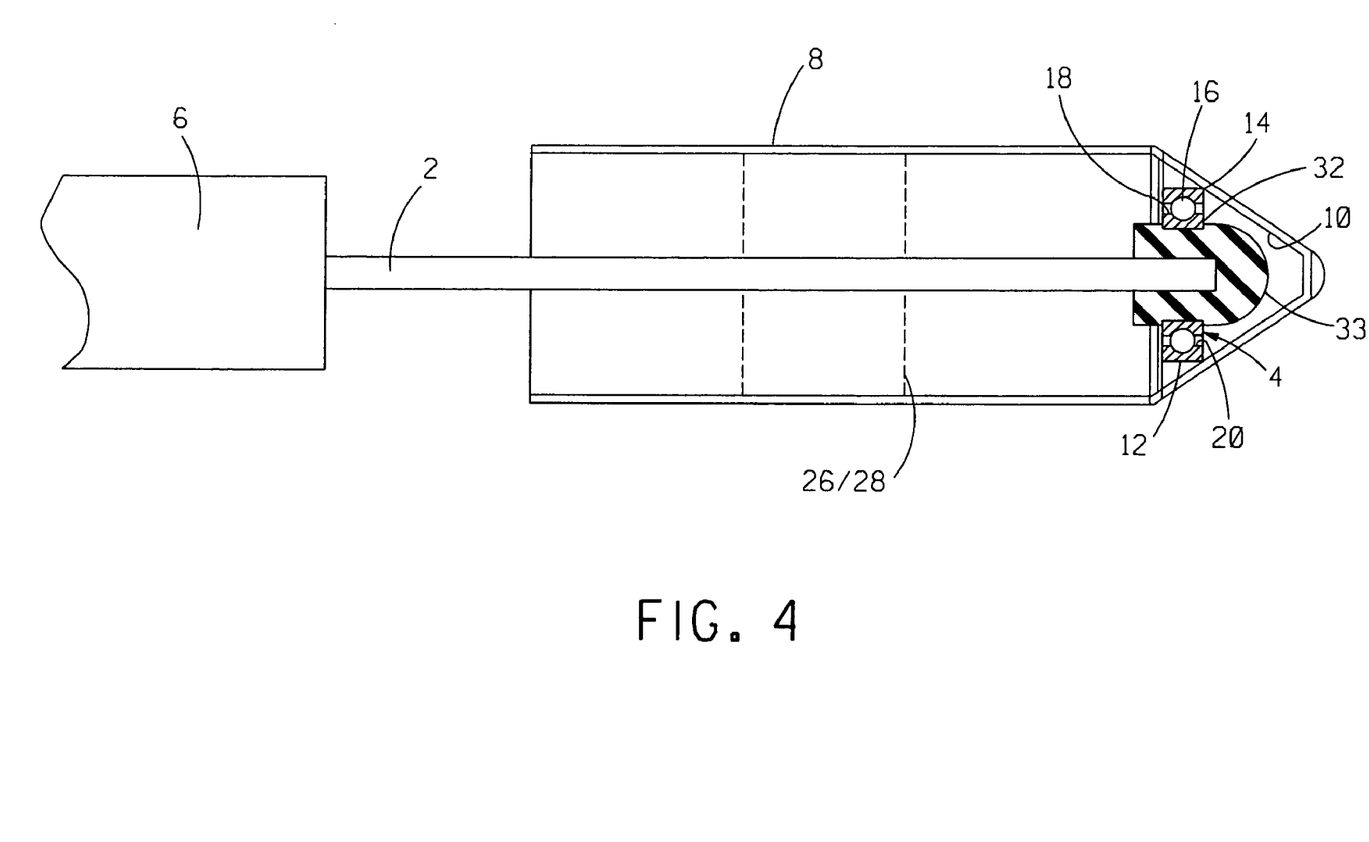
FIG. 4 is a cross section of the vial and ball bearing shown in FIGS. 2 and 3.
Figure 5:
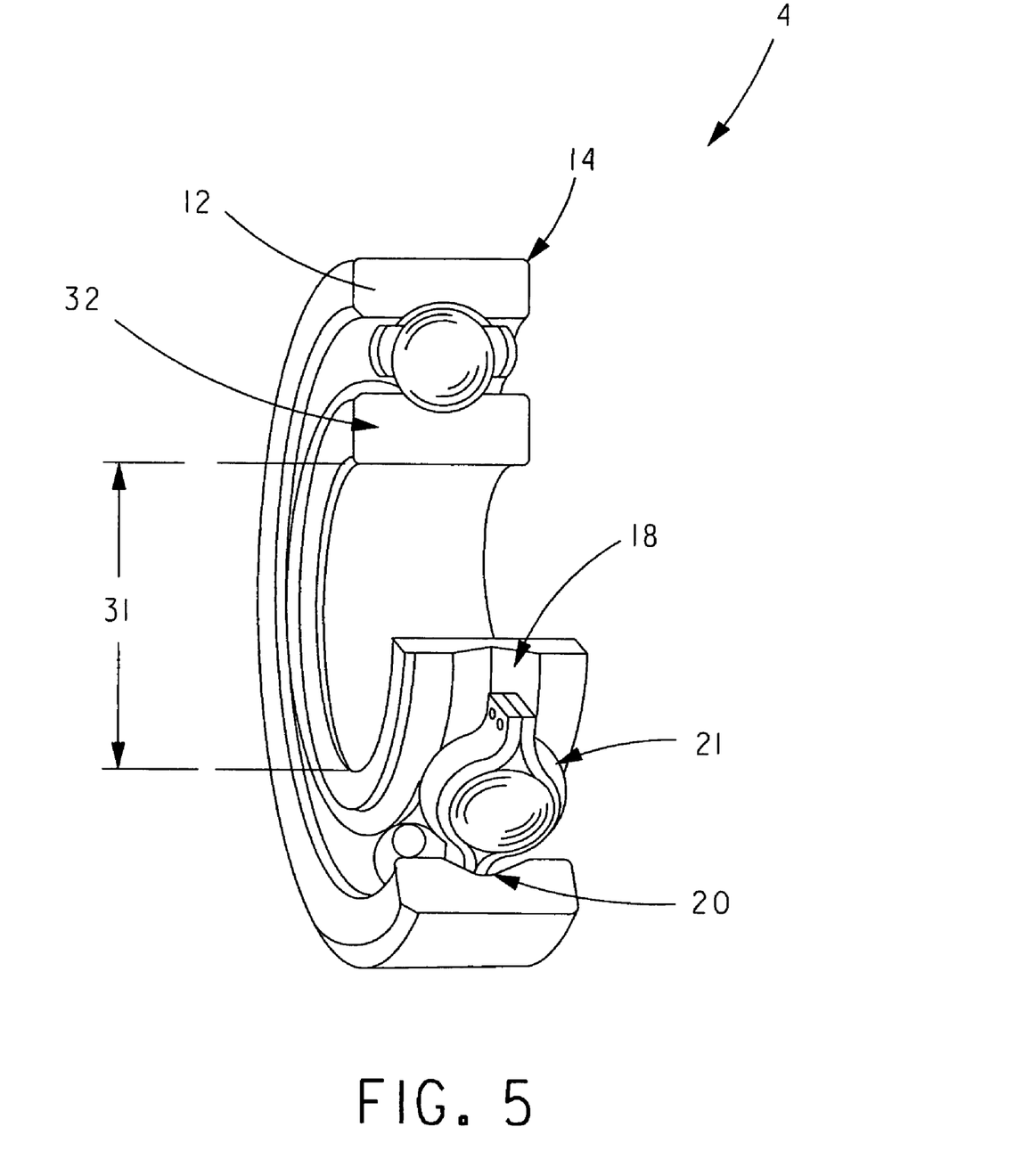
FIG. 5 is an isolated perspective view of a cross section of the ball bearing shown in FIGS. 1-4.

The axial force applied to shaft 2 to produce the frictional contact between corner radius 14 of outer ring 12 and the conical or concave-shaped surface of bottom wall 10 also produces contact between opposed inner and outer bearing races or surfaces 18 and 20 of inner and outer rings 32 and 12, respectively, of ball bearing 4 and the rolling elements or balls 16 of ball bearing 4 that maintain bearing races 18 and 20 in spaced relation. This contact results in a configuration and geometry that enables effective crushing of a sample material in the manner to be described hereinafter.

Ball bearing 4 can include one or more optional separators 21 around one or more balls 16 of ball bearing 4 for maintaining separation between adjacent balls 16 whereupon, in use of ball bearing 4, impact is avoided between balls 16, which can cause undesirable particulates of material to be generated from balls 16 and introduced into the sample. Such undesirable particulates can result in the generation of false or erroneous signals during measurement of the broken up sample material. Any suitable and/or desirable bearing configuration, such as, without limitation, a needle bearing or a roller bearing, can be used to generate the grinding action to be discussed hereinafter, but ball bearing 4 shown in FIGS. 1-5 is desired due to its simplicity, effectiveness and low cost.

Desirably, drive mechanism 6 is configured to drive shaft 2 rotationally to a relatively high angular velocity. Although a single direction of rotation at constant RPM may be utilized, drive mechanism 6 is desirably reversible and capable of driving shaft 2 in both directions, one direction at a time. High speed rotation of shaft 2 in one direction has been observed to cause a fluid 22 disposed in vial 8 in which one or more sample particle(s) 24 under test is/are received to spin with shaft 2, thereby forming a vortex that can pull or draw air into fluid 22. Once such air reaches bearing 4, it is broken into small bubbles, thereby causing undesirable foaming of fluid 22. Reversal of the direction of rotation of shaft 2 on a periodic or as-needed basis helps avoid the forming of the vortex and, thereby, the drawing of air into fluid 22 and, consequently, such undesirable foaming.

Figure 6:
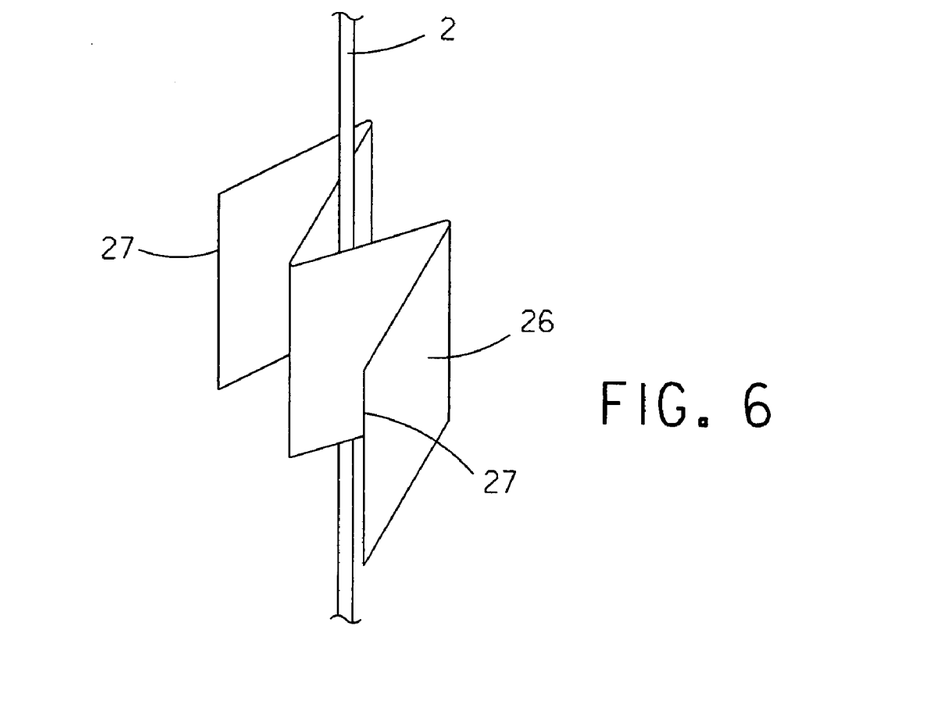
FIGS. 6 and 7 are first and second embodiment baffles that can be inserted into the vial shown in FIGS. 2-4 to avoid rotation of the fluid in the vial and, hence, the introduction of air into the fluid.
Figure 7:
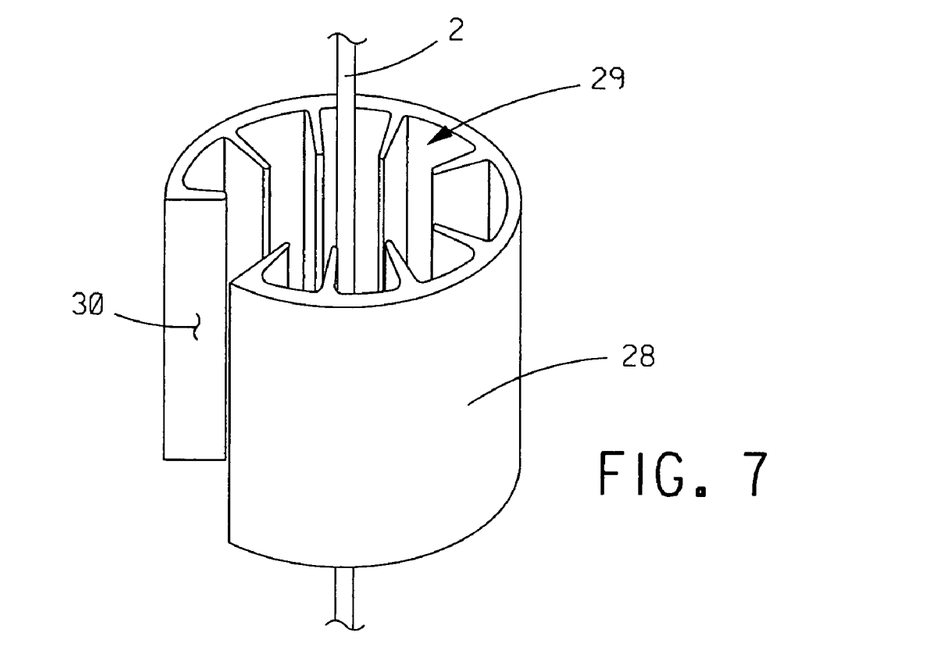

Also or alternatively, vortex formation and the drawing of air into fluid 22 and the resulting undesirable foaming problem can be avoided by use of a baffle in vial 8 during the grinding process. A first embodiment baffle 26, shown in FIG. 6, can be made out of a strip of material folded into any suitable shape, such as the W shape shown, which is then inserted into vial 8 around shaft 2. Desirably, baffle 26 is formed of a material that has a spring action that presses edges 27 of baffle 26 into frictional contact with the interior wall of vial 8 when baffle 26 is positioned in vial 8. A second embodiment baffle 28, shown in FIG. 7, has a cylindrical form with an internal gear-shaped structure 29 and an elongated slot 31. In use, second embodiment baffle 28 is inserted into vial 8 with shaft 2 positioned within internal gear-shaped structure 29. Desirably, baffle 28 has a spring action that presses against and produces friction between an exterior of wall baffle 28 and the interior wall of vial 8 when baffle 28 is positioned in vial 8. An exemplary position of baffle 26 or 28 in vial 8 is shown in phantom in FIG. 4. Desirably, baffle 26 and/or 28 is made of material(s) that will not contaminate fluid 22 or sample 24 during grinding of sample 24. The foregoing description of baffle 26 and baffle 28 is not to be construed as limiting the invention since it is envisioned that any suitable and/or desirable baffle configuration that avoids formation of the vortex, and thereby the drawing of air into fluid 22 and consequently undesirable foaming of fluid 22, is envisioned.

There are various methods of mounting ball bearing 4 to shaft 2. In the simplest configuration, shaft 2 is press fit directly into a bore 30, shown best in FIG. 5, of inner ring 32 of ball bearing 4 where it is held in place by friction. Alternatively, shaft 2 is of minimum practical diameter and is mounted to bore 30 of inner ring 32 of ball bearing 4 by way of a bushing 33, shown best in FIG. 4. Desirably, bushing 33 is made of vibration-absorbing material, such as polyurethane. However, other polymeric materials can be used, if desired, because of their inherent cleanliness or chemical inertness.

Drive mechanism 6 can be permanently or removably mounted to shaft 2. Desirably, shaft 2 is mounted to drive mechanism 6 by way of a chuck (not shown) that allows quick removal of shaft 2 from drive mechanism 6. Such approach allows sterilization and cleaning of shaft 2.

In accordance with the present invention, grinding of biological sample particles 24, such as mold sample particles, suspended in fluid 22 disposed in vial 8 is accomplished by a crushing action between two relatively hard surfaces making contact. Specifically, in the present invention, grinding of sample 24 is accomplished by the moving contact between two surfaces, where one is rolling over the other. More specifically, having drive mechanism 6 rotate shaft 2 causes inner ring 32 to rotate in concert with shaft 2, while outer ring 12 is held stationary by the frictional interaction of corner radius 14 of outer ring 12 in contact with the surface of bottom wall 10. The rotation of inner ring 32 relative to stationary outer ring 12 causes balls 16 to roll between rotating race 18 of inner ring 32 and race 20 of outer ring 12, which is held stationary by the frictional interaction between corner radius 14 of outer ring 12 in contact with the inner surface of bottom wall 10.

Since balls 16 are round, one or more gaps 34 (shown best in FIG. 1) exist between adjacent balls 16. During rotation of shaft 2, sample particles 24 suspended in fluid 22 enter into said one or more gaps 34, whereupon sample particles 24 are crushed or ground between one or more rolling balls 16 and one or both of races 18 and 20.

Desirably, ball bearing 4 is used as the grinding element. However, this is not to be construed as limiting the invention. Rolling action between balls 16 and races 18 and 20 results in continuous feed of sample particles 24 into the one or more gaps 34 and continuous crushing of sample particles 24. The construction of ball bearing 4, especially with one or more optional separators 21, avoids impact forces that can damage the surface(s) of balls 16, race 18 and/or race 20 with resulting wear and debris that may affect the results of the measurement of the broken up or crushed sample particles 24. In comparison with devices based on friction or impact, the amount of debris produced by the present invention is reduced significantly.

Figure 8:
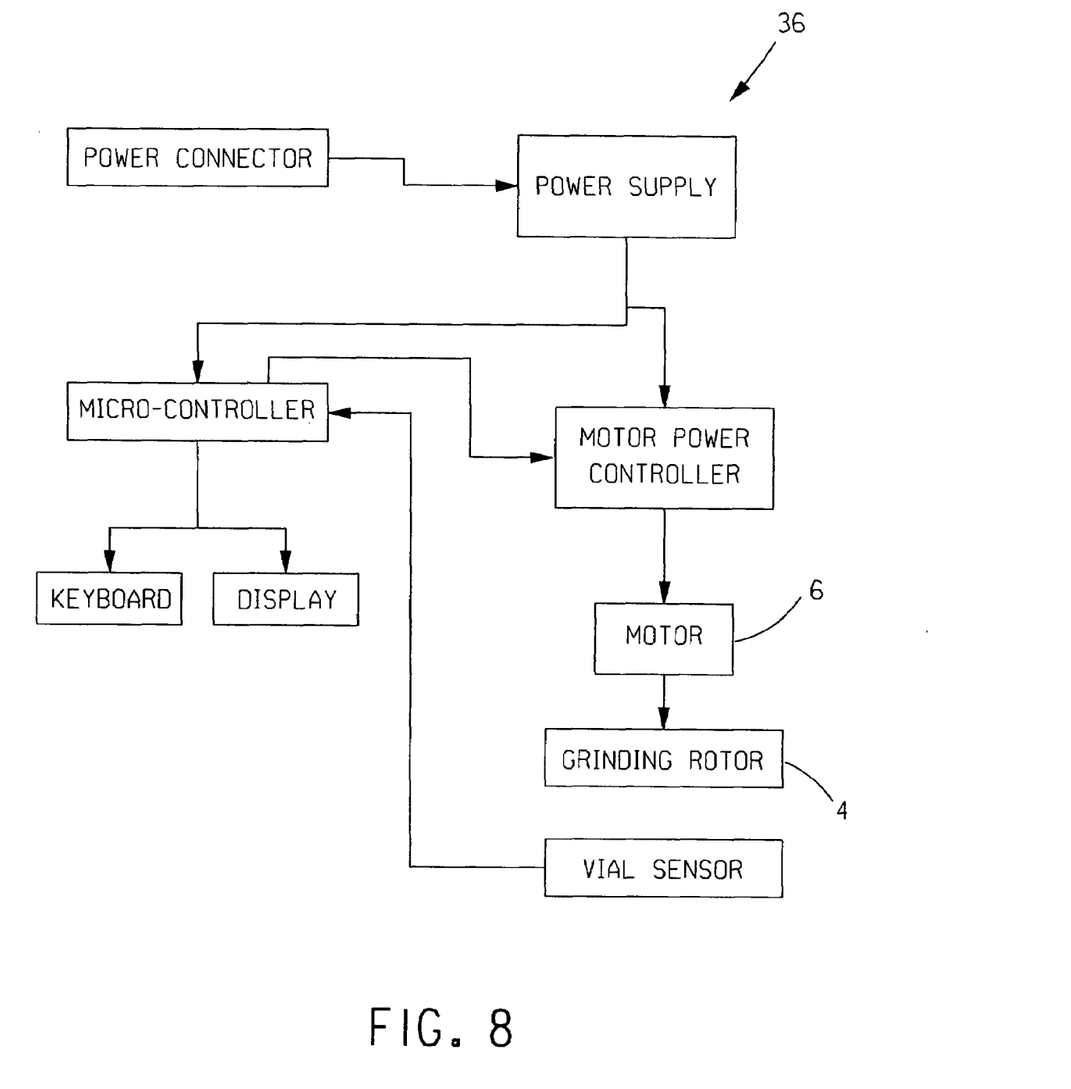
FIG. 8 is a block diagram of the components forming an exemplary sample preparation system in accordance with the present invention.

FIG. 8 shows a schematic block diagram of an exemplary sample preparation system 36 that incorporates the combination of bearing 4, shaft 2, drive mechanism 6 and vial 8 described above.

Figure 9:
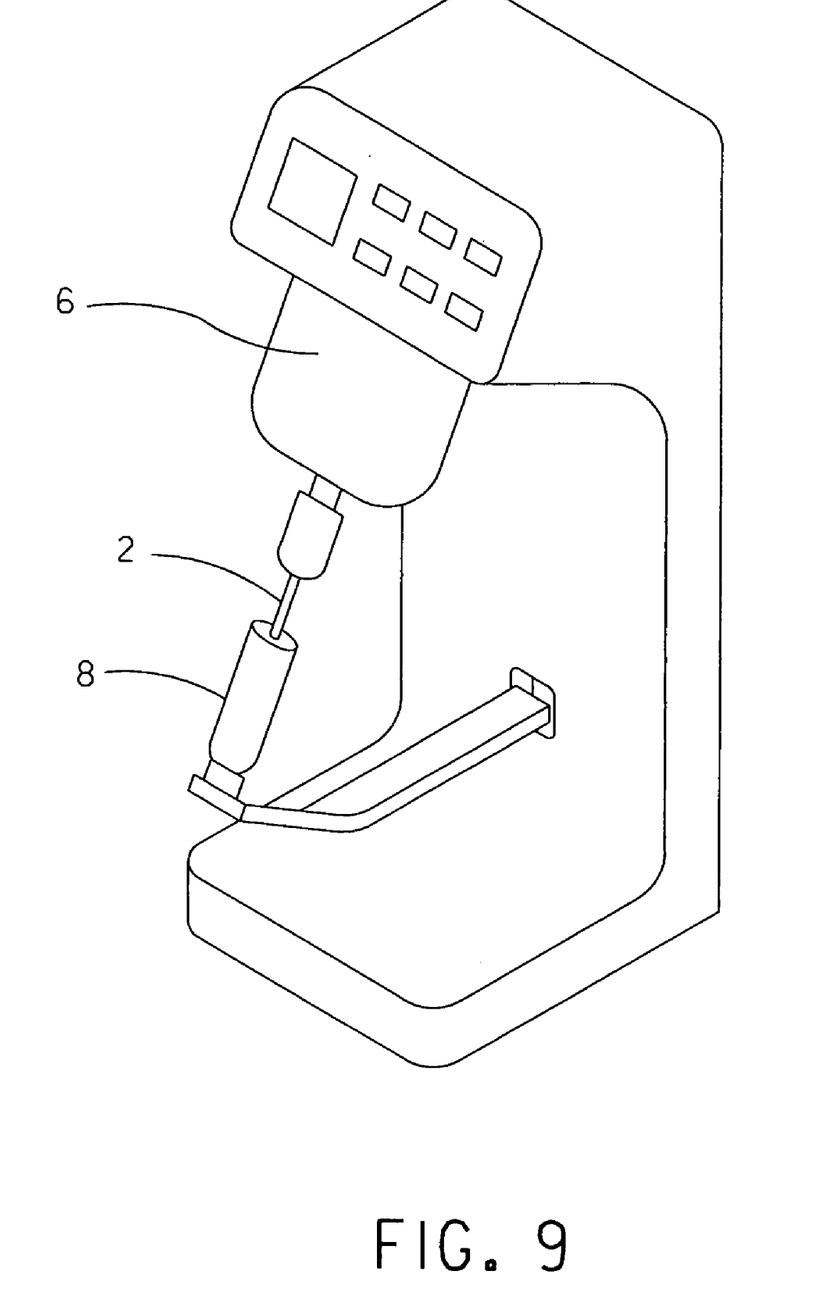
FIG. 9 is a perspective view of an exemplary housing for housing the various components of the exemplary sample preparation system shown in FIG. 8.

Lastly, FIG. 9 shows perspective view of an exemplary housing for housing the various components of the sample preparation system 36 of FIG. 8 and for supporting shaft 2 within vial 8 during grinding of sample 24.

The invention has been described with reference to the preferred embodiment. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A biological sample grinding device comprising:
a vial having a conical or concave interior surface;
a shaft; and
a bearing having a plurality of rolling elements disposed between a pair of surfaces in contact therewith, said rolling elements defining at least one gap therebetween, said bearing mounted to said shaft and disposed in said vial such that one surface of said bearing is rotatable in concert with said shaft while the other surface of said bearing is held stationary against the rotation of said shaft via said interior surface of said vial, wherein at least one biological sample particle disposed in a fluid in which said bearing is submerged in said vial enters the at least one gap between said rolling elements whereupon, in response to rotation of said shaft, said biological sample is subject to being crushed or ground between at least one rolling element and at least one of said pair of surfaces.

2. The device of claim 1, wherein said bearing is a ball bearing, a needle bearing or a roller bearing.

3. The device of claim 1, further including means for rotating said shaft and the one surface of said bearing about a longitudinal axis of said shaft.

4. The device of claim 1, further including a baffle disposed in said vial, said baffle operative during rotation of said shaft and the one surface of said bearing for inhibiting the rotation of the fluid.

5. The device of claim 4, wherein the baffle is either (1) a sheet having at least one fold or (2) at least a partial cylinder having a plurality of inwardly extending projections.

6. The device of claim 1, wherein said bearing includes a bore which is press fit to said shaft to mount said bearing to said shaft.

7. The device of claim 1, wherein each surface of said bearing is defined by a race formed in a ring of said bearing.

8. A method of grinding a biological sample comprising:
(a) providing a container;
(b) inserting a bearing in said container, said bearing having a plurality of rolling elements disposed between a pair of rings of said bearing;
(c) introducing a fluid having at least one biological sample particle therein into said container; and
(d) with said bearing immersed in said fluid having the biological sample particle therein, causing one ring of said bearing to rotate relative to the other ring of said bearing such that the rolling elements roll between the pair of rings whereupon, in response to said rotation, the biological sample particle is drawn by the fluid between the pair of rings where it is subject to being crushed or ground between at least one of said rolling elements and at least one of said rings.

9. The method of claim 8, wherein step (d) includes reversing the rotation direction of the one ring of said bearing at least one time.

10. The method of claim 8, wherein:
the one ring is an inner ring of said bearing; and
the other ring is an outer ring of said bearing which is held stationary in said container.

11. The method of claim 10, wherein the outer ring of said bearing is held stationary in said container via an interior wall of said container.

12. The method of claim 10, wherein the outer ring of said bearing is held stationary in said container via frictional interaction between said outer ring and an interior wall of said container.

13. The method of claim 8, further including inserting a baffle in said container, said baffle operative for avoiding the introduction of air into the fluid in response to the rotation of the one ring of said bearing relative to the other ring of said bearing.

14. The method of claim 13, wherein the baffle is either (1) a sheet having at least one fold or (2) at least a partial cylinder having a plurality of inwardly extending projections.

15. A biological sample grinding device comprising:
a vessel for receiving a fluid having at least one biological sample particle therein;

a bearing disposed in said vessel, said bearing having a plurality of rolling elements disposed for rolling between a pair of coaxial, radially opposed surfaces; and means for rotating one of said bearing surfaces relative to the other of said bearing surfaces when said bearing is submerged in the fluid received in the vessel whereupon, in response to said rotation, the biological sample particle is drawn by the fluid between the pair of surfaces where the biological sample particle is crushed or ground between at least one of the rolling elements and one of the pair of surfaces.

16. The device of claim 15, wherein:

the pair of surfaces includes a first surface that faces radially outward and a second surface that faces radially inward;

the means for rotating rotates the first surface; and the second surface is maintained stationary via a wall of the vessel when the means for rotating is rotating the first surface.

17. The device of claim 16, further including a baffle disposed in said vessel and operative for inhibiting the introduction of air into the fluid during rotation of the first surface.

18. The device of claim 16, wherein the means for rotating reverses the direction of rotation of the first surface at least one time.

19. The device of claim 16, wherein the means for rotating includes a motor driven shaft coupled to a ring that defines the first surface.

20. The device of claim 16, wherein:

the vessel has a conical or concave interior surface;

a ring defines the second surface; and a part of the ring other than the second surface frictionally engages the conical or concave interior surface, thereby avoiding rotation of the second surface when the means for rotating rotates the first surface.

* * * * *